(12) United States Patent
Warren et al.

(10) Patent No.: US 6,482,991 B2
(45) Date of Patent: Nov. 19, 2002

(54) METHOD AND APPARATUS FOR THE PREPARATION OF ALDEHYDES

(75) Inventors: Jack S. Warren, Blountville, TN (US); David R. Westphal, Chanhassen, MN (US); Steve J. Zoubek, Otsego, MN (US)

(73) Assignee: EagleView Technologies, Inc., Minneapolis, MN (US)

( * ) Notice: Subject to any disclaimer, the term of this patent is extended or adjusted under 35 U.S.C. 154(b) by 0 days.

(21) Appl. No.: 09/974,189

(22) Filed: Oct. 9, 2001

(65) Prior Publication Data

US 2002/0143213 A1 Oct. 3, 2002

Related U.S. Application Data

(60) Provisional application No. 60/279,850, filed on Mar. 29, 2001.

(51) Int. Cl.[7] .................................................. C07C 45/36
(52) U.S. Cl. ........................................ 568/431; 568/436
(58) Field of Search ................................. 568/431, 436

(56) References Cited

U.S. PATENT DOCUMENTS

| 3,948,995 | A | | 4/1976 | Jouffret |
| 3,948,998 | A | | 4/1976 | Fujiyama et al. |
| 4,195,040 | A | | 3/1980 | Renner |
| 4,218,403 | A | | 8/1980 | Vanderpool |
| 4,554,383 | A | | 11/1985 | Knifton |
| 5,475,156 | A | * | 12/1995 | Caruso et al. ............... 568/780 |
| 5,679,867 | A | | 10/1997 | Bruce et al. |
| 5,877,330 | A | | 3/1999 | Kishimoto et al. |
| 5,910,613 | A | | 6/1999 | Schiraldi et al. |

FOREIGN PATENT DOCUMENTS

DE          19946590       *  5/2001

* cited by examiner

*Primary Examiner*—Sreeni Padmanabhan
(74) *Attorney, Agent, or Firm*—Popovich & Wiles, P.A.

(57) ABSTRACT

A method and an apparatus for producing aromatic aldehydes, including benzaldehyde and metatolualdehyde wherein the reaction occurs in the vapor phase. Raw materials and a source of oxygen are fed into a tube reactor. The raw materials may be in a liquid or vapor phase. The reaction to form the aldehyde is catalyzed by suitable solid or liquid catalysts, including copper containing catalysts.

18 Claims, 1 Drawing Sheet

METHOD AND APPARATUS FOR THE PREPARATION OF ALDEHYDES

This application claims the benefit of provisional application Ser. No. 60/279,850, filed Mar. 29, 2001, the contents of which are hereby incorporated herein by reference.

FIELD OF THE INVENTION

The present invention relates generally to the preparation of aldehydes and more particularly to a method and apparatus for preparing aromatic aldehydes from aromatic compounds.

BACKGROUND OF THE INVENTION

In general, aromatic aldehydes are useful as organic and chemical intermediates, as gas and oil additives, and as flavoring and fragrance agents, among others. More specifically, benzaldehyde has been used in the production of maraschino cherries and artificial jasmine odor, among others.

A variety of processes exist in the prior art for producing aromatic aldehydes from a corresponding aromatic compound. Many involve reacting the aromatic compound with carbon monoxide in the presence of various catalysts. For example, U.S. Pat. No. 3,948,998 (Fujiyama et al.) discloses a process for producing p-tolualdehyde by reacting toluene with carbon monoxide in the presence of a hydrogen fluoride-boron trifluororide catalyst. In U.S. Pat. No. 4,218,403 (Vanderpool), an alkyl-substituted phenyl aldehyde is prepared by reacting an alkyl-substituted benzene with carbon monoxide under super atmospheric pressure in the presence of a catalyst. U.S. Pat. No. 5,679,867 (Bruce et al.) discloses a process for making tolualdehyde by carbonylating toluene with either carbon monoxide or a source of carbon monoxide in a system free of hydrogen chloride and with a special catalyst. U.S. Pat. No. 5,910,613 (Schiraldi et al.) also discloses a process for producing aromatic aldehydes via carbonylation using triflic acid as a catalyst.

U.S. Pat. No. 4,554,383 (Knifton) discloses a method for preparing an aromatic aldehyde utilizing a "melt" catalyst system comprising aluminum halide-alkyl pyridinium as well as various other prior art processes for producing aromatic aldehydes.

U.S. Pat. No. 5,877,330 (Kishimoto et al.) discloses the use of vanadium-containing catalysts for use in various types of oxidation reactions including oxidation reactions of aromatic hydrocarbons and various other compounds.

Despite the existence of a variety of methods for producing aromatic aldehydes from their corresponding aromatic compounds, there is a continuing need in the art for cost effective methods of producing aromatic aldehydes.

SUMMARY OF THE INVENTION

The present invention relates to a method and an apparatus for producing aromatic aldehydes such as benzaldehyde and metatolualdehyde, among others. Specifically, the method and apparatus of the present invention utilizes readily available and inexpensive raw materials, results in high conversion and selectivity rates, and thus provides increased production of the desired aldehyde. Generally, the raw materials used in the method and apparatus of the present invention include an aromatic compound and a source of oxygen, such as oxygen gas.

In one aspect, this invention is a process for the production of an aldehyde comprising providing a compound of formula $R^1$—CX, wherein X is a group that leaves upon oxidation; reacting $R^1$—CX and a source of oxygen to form $R^1$—COH, wherein the reacting occurs in the liquid or vapor phase at a temperature of from 100° C. to 200° C. and in the presence of a catalyst consisting essentially of one or more of copper oxide and copper esters, wherein $R^1$ is phenyl, which is unsubstituted or substituted by one or more identical or different radicals selected from $(C_1$-$C_{12})$-alkyl, $(C_1$-$C_{12})$-alkoxy, $(C_1$-$C_{12})$-alkanoyloxy, $(C_1$-$C_{12})$-alkanoyl, amino, hydroxyl, —$CH_2$—O—$(C_1$-$C_{12})$-alkyl, —NH—$(C_1$-$C_{12})$-alkyl, —NH—CO—$(C_1$-$C_{12})$-alkyl, or —S—$(C_1$-$C_{12})$alkyl; and separating the $R^1$—COH.

Preferably, the source of oxygen is oxygen gas. The catalyst may be a liquid or a solid and is preferably cuprous oxide on a zirconia support. In a more preferred embodiment, the catalyst is a monolayer of cuprous oxide on a zirconia support. The cuprous oxide may be present at 2 to 20% by weight, or, more preferably, 2 to 10% by weight. The catalyst also may be selected from copper octoate and copper acetate. X may be —$H_3$, and $R^1$ may be meta-methylphenyl. The reacting may be in the vapor phase and may be in one tube reactor or two or more tube reactors connected in parallel. The process may also include stopping the reaction of $R^1$—CX and the source of oxygen in a first of the two or more tube reactors while passing the $R^1$—CX and the source of oxygen through a second of the two or more tube reactors and regenerating the catalyst in the first tube reactor. The process may be continuous.

In a second aspect, this invention is method of preparing metatolualdehyde that includes providing meta-xylene and a source of oxygen; providing a tube reactor loaded with a catalyst consisting essentially of one or more of copper oxide and copper esters; passing the meta-xylene and the source of oxygen through the tube reactor at a temperature of between about 100° C. and 200° C.; and recovering the metatolualdehyde.

In a third aspect, this invention is a method of preparing benzaldehyde that includes providing toluene and a source of oxygen; providing a tube reactor loaded with a catalyst consisting essentially of one or more of copper oxide and copper esters; passing the toluene and the source of oxygen through the tube reactor at a temperature of between about 100° C. and 200° C.; and recovering the benzaldehyde.

In a fourth aspect, this invention is a process for the production of an aldehyde comprising providing a compound of formula $R^1$—CX, wherein X is a group that leaves upon oxidation; reacting $R^1$—CX and a source of oxygen to form $R^1$—COH, wherein the reacting occurs in the liquid or vapor phase at a temperature of from 100° C. to 200° C., at a weight hourly space velocity of greater than one, and in the presence of a catalyst, wherein $R^1$ is phenyl, which is unsubstituted or substituted by one or more identical or different radicals selected from $(C_1$-$C_{12})$-alkyl, $(C_1$-$C_{12})$-alkoxy, $(C_1$-$C_{12})$-alkanoyloxy, $(C_1$-$C_{12})$-alkanoyl, amino, hydroxyl, —$CH_2$—O—$(C_1$-$C_{12})$-alkyl, —NH—$(C_1$-$C_{12})$-alkyl, —NH—CO—$(C_1$-$C_{12})$-alkyl, or —S—$(C_1$-$C_{12})$-alkyl; and separating the $R^1$—COH.

DETAILED DESCRIPTION OF THE PREFERRED EMBODIMENTS

Figure 1:
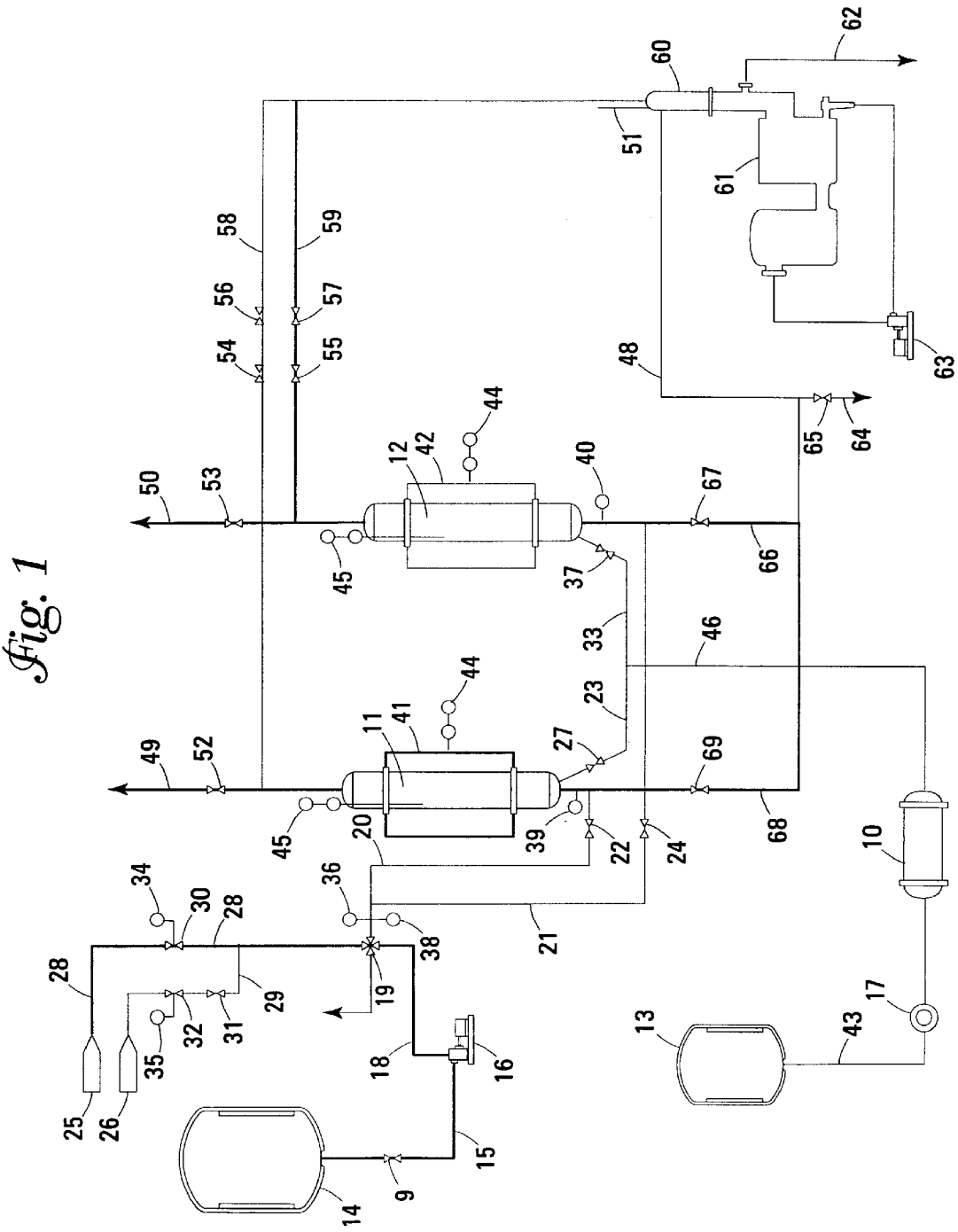
FIG. 1 is a schematic illustration of the method and apparatus of the present invention.

More specifically, the present invention involves the preparation of aromatic aldehydes involving the oxidation of an aromatic compound in a tube reactor provided with a suitable catalyst. The preferred raw materials or feed materials include an aromatic compound and a source of oxygen. These materials are fed into a catalytic tube reactor where they are exposed to the catalyst and react to produce the desired aldehyde. Preferably, the raw materials are fed from the bottom of the reactors to the top so that the reactant materials flow vertically upwardly through the reactor.

To minimize downtime of the production process during the regeneration of catalyst or during reactor maintenance or repair, multiple or side-by-side reactors are provided with means for selectively directing the reactant materials to one or the other of the reactors and removing product and recycle streams from such selected reactor. This permits the non-selected reactor or reactors to be repaired and/or maintained and the catalyst therein to be regenerated, if needed.

The apparatus and method of this invention are applicable to a wide variety of aldehydes and more specifically to aromatic aldehydes. The aldehydes are formed by the catalyzed reaction of $R^1$—$CH_3$ to $R^1$—COH in the presence of a source of oxygen. $R^1$ is phenyl, which may be unsubstituted or substituted by one or more identical or different radicals selected from $(C_1-C_{12})$-alkyl, $(C_1-C_{12})$-alkoxy, $(C_1-C_{12})$-alkanoyloxy, $(C_1-C_{12})$-alkanoyl, amino, hydroxyl, —$CH_2$—O—$(C_1-C_{12})$-alkyl, —NH—$(C_1-C_{12})$-alkyl, —NH—CO—$(C_1-C_{12})$-alkyl, or —S—$(C_1-C_{12})$-alkyl.

In the most preferred embodiments, $R^1$ includes phenyl and methyl phenyl, that is, the preferred aldehydes include benzaldehyde and toluadehyde, respectively.

The source of oxygen preferably is oxygen gas ($O_2$), however, other sources of oxygen, such as water, hydrogen peroxide ($H_2O_2$), ozone ($O_3$), oxygen enriched inert gas or oxygen enriched water vapor and other suitable sources such as are known to those of skill in the art may be used.

Useful catalysts in the practice of this invention include solid phase (heterogeneous) and liquid phase (homogeneous) catalysts as described further below. Heterogeneous catalysts typically include a support that has been impregnated with a catalyst. In a preferred embodiment, also described further below, the catalyst is present in a monolayer on a support material.

Turning now to FIG. 1, a preferred embodiment of the method and apparatus of this invention is illustrated. The preferred method is described with respect to metatolualdehyde. Unless otherwise indicated all percentages are by weight.

FIG. 1 illustrates that the primary reaction members comprise a pair of vapor phase tube reactors 11 and 12. If desired or needed, more than two reactors could be provided to accommodate the specific reaction time or life cycle of the selected feed material and the regeneration time of the selected catalyst. Reactors 11 and 12 are preferably conventional stainless steel catalytic tube reactors filled with various combinations of inert filler material and catalyst. Inert filler material may comprise glass beads between about 3 to 10 millimeters (mm) in diameter, or may include one or more of stainless steel beads, lava rock and sand. If the catalyst is a liquid phase catalyst, i.e., homogeneous, the tube reactor is filled only with an inert material, preferably glass beads. The inert filler material prevents laminar flow and promotes both turbulent flow and uniform exposure to the catalyst.

If the catalyst is a heterogeneous catalyst, at least a portion of the reactor is filled with a catalytic material. The tube reactors also may contain inert filler material. Suitable solid phase catalysts include metal oxides. Preferred metal oxides include MgO, $TiO_2$, $ZrO_2$, ZnO, CuO, $Cu_2O$, $CeO_2$, $Ce_2O_3$, other lanthanide oxides, mixtures of these oxides, and naturally occurring clay material such as montmorillonite or kaolin. More preferred catalysts contain copper. The most preferred catalysts are CuO (cuprous oxide) and $Cu_2O$ (cupric oxide) in a monolayer on $ZrO_2$ (zirconium oxide) support material.

Suitable liquid phase catalysts include metal compounds that are soluble in the starting material or suitable solutions of metal compounds. The liquid phase catalysts may be used at concentrations ranging from 200 to 2000 ppm. Preferred catalysts include esters of copper and cerium such as the acetates and octoates. For example, copper octoate and copper acetate are suitable esters. Other suitable homogeneous catalysts include soluble metal compounds selected from groups IB to VIIIB of the periodic table, i.e., salts of the transition metals, including such compounds as nitrates, perchlorates, halides, and sulfates. Soluble metallocenes may also be suitable.

Catalyst preparation is discussed in greater detail below.

The catalyst loading (i.e., the concentration of the catalyst on the solid support) is preferably in the range of 2 to 20 percent weight, with a more preferred range being 2 to 10 percent by weight. For example, a monolayer of a preferred catalyst, CuO on $ZrO_2$, has a loading of about 2.4%. Such a catalyst range, however, will vary with the particular catalyst and catalyst support and support configuration being used, as known to one of skill in the art.

The distribution of the catalyst within reactors 11 and 12 can vary, also as known to one of skill in the art. For example, the bottom third of the reactor can be filled with inert material in the form of glass beads, the middle third of the reactor can be filled with catalyst and the top third of the reactor can be filled with inert material in the form of glass beads.

In the preferred embodiment illustrated in FIG. 1, reactors 11 and 12 are vertically oriented so that the feed materials pass vertically upwardly from the bottom to the top of the reactors. However, the benefits of the invention can also be realized with reactors having different orientations so that the feed materials flow downwardly or laterally through the reactors. However, these latter orientations are not as preferred.

The raw or reactive material in accordance with the present invention is provided from a reactant material source or reservoir 14. In general, the reactant or feed material will comprise an aromatic compound. For the production of benzaldehyde, this feed material will comprise toluene, while for the production of metatolualdehyde, the feed material will comprise meta-xylene (i.e., $R^1$ is meta-methylphenyl).

The feed material is fed from reservoir 14 through conduit 15, fitted with valve 9, to pump or pressure member 16 which discharges the feed material into conduit 18 at a pressure greater than atmospheric. The pressure is selected to optimize the reaction conditions (conversion and selectivity) and to maintain the feed materials in a liquid or vapor phase at the selected reaction temperature. In the preferred method and apparatus, the feed material is pressurized to a range of about 5 to 500 psig (34 to 3447 MPa), and more preferably to a pressure of about 100 psig to 450 psig (689 to 3102 MPa). Most preferably, the pressure is provided at about 300 psig to 400 psig (2068 to 2757 MPa).

From pump or pressure member 16, the feed material is directed through conduit 18 to valve complex 19, which selectively directs the feed material either to reactor feed conduit 20 or 21. As shown, feed conduits 20 and 21 are connected respectively, to the bottom ends of reactors 11 and 12. Reactor feed conduits 20 and 21 include shutoff valves 22 and 24, respectively, for isolating reactors 11 and 12 from the feed materials and for facilitating the flow of purging or other materials, if desired. If more than two reactors are utilized, valve complex 19 is modified and additional reactor feed conduits and shutoff valves are provided so that the flow of the feed materials can be selectively directed to each reactor, while selectively isolating one or more of the others.

To facilitate oxidation of the feed material in reactors 11 and 12, a source of oxygen (e.g., oxygen gas ($O_2$)) is provided in reservoir 13.

During the process, oxygen is fed from reservoir 13 via conduit 43 through feed regulator 17 which delivers pressurized oxygen to reactors 11 and/or 12 through conduits 23 and 33, respectively. Heater 10 is provided and is used as desired to heat the oxygen as it flows through conduit 43. The source of oxygen exits heater 10 via conduit 46, which intersects conduits 23 and 33. Valves 27 and 37 are provided in conduits 23 and 33, respectively, to isolate and regulate the oxygen source during purging, maintenance or when otherwise desired.

The system of the present invention also includes a supply of purging and/or regeneration gases such as air/$O_2$/$N_2$. In the preferred embodiment, reservoirs 25 and 26 contain air and nitrogen, respectively, although other materials known in the art can be used as well such as hydrogen and methane. The regeneration materials are used during purging or preheating of reactors 11 or 12 or during regeneration of the catalyst is within reactors 11 and 12. The air and nitrogen from reservoirs 25 and 26 are provided to valve 19 through conduits 28 and 29, respectively. Conduits 28 and 29 are also provided with a plurality of shut-off valves 30, 31 and 32 to selectively control the flow of regeneration gases to valve 19. Pressure regulators 34 and 35 are associated with valves 30 and 32. Valve 19 functions to selectively direct the flow of materials 25 and/or 26 to either the reactor feed conduit 20 or the reactor feed conduit 21. Conduits 20 and 21 are provided with temperature gauges 36 and 38, respectively, upstream of valves 22 and 24, and temperature gauges 39 and 40 downstream of valves 22 and 24, respectively.

Reactors 11 and 12 are also provided with heating means 41 and 42. Controller/regulator 44 is provided for each heater 41 and 42 and selectively controls heaters 41 and 42. Means for monitoring the temperature and pressure within the reactor are also provided on each reactor 11 and 12 in the form of pressure and temperature monitors 45.

Outflow or product exit conduits 49 and 50 are connected with the top or upper ends of reactors 11 and 12, respectively, for directing the outflow from the reactors to conduits 58 and 59, respectively, and thence to product separation means 61. Exit conduits 49 and 50 each are equipped with valves 52 and 53, respectively, which are opened when desired to purge the reactors. Conduits 58 and 59 are provided with back pressure regulator valves 54 and 55, respectively, and additional valves 56 and 57 for control of the flow of the product stream. If more than two reactors are provided, additional exit conduits, waste conduits and associated valves are also provided.

Product recovery means 61 (including a reboiler (not shown), a receiver (not shown), precipitation or distillation column 60 and pressure means or pump 63) recovers the preferred product, namely, the desired aromatic aldehyde (such as benzaldehyde or metatolualdehyde) from the exit stream. Distillation column 60 also is provided with vent 51. FIG. 1 shows that the desired aromatic aldehyde is recovered via conduit 62, with any unreacted materials (i.e., unoxidized feed material) may be recycled to reactors 11 or 12 through conduit 48. If a recycle is not desired, the remaining materials may be recovered through conduit 64 provided with valve 65.

Having described the apparatus and system of the present invention in detail, the aldehyde production method may be understood best as follows. First, one of reactors 11 and 12 is selected for initial use in the process of the present invention. For purposes of describing the preferred method of the present invention, reactor 11 will be selected. In such case, reactor 12 is isolated from the system by closing valves 24, 53 and 55. Reactor 11 is then prepared for preparation of the aldehyde, specifically benzaldehyde or metatolualdehyde, by activating heater 41 and providing a purging gas from sources 25 and/or 26, through valve 19 and into the lower end of reactor 11. At this time, oxygen supply valves 27 and 37 are closed. In accordance with the preferred embodiment, reactor 11 is preferably preheated by heater 41 to a temperature in the range of 50° C. to 400° C. and more preferably in the range of 100° C. to 200° C. Most preferably the preferred reaction temperature is first determined and the reactor is heated to this temperature. This preferred temperature will vary to some extent with the composition of the feed stream, the concentration and type of catalyst, the liquid or weight hourly space velocity at which the reactor will be run, etc. Reactor 11 is then heated to this preferred temperature.

When the preferred temperature is reached, valve 19 is actuated to stop the flow of the purging or other gas to reactor 11 and to provide feed material of the desired composition from reservoir or source 14. This pressurized feed stream is supplied to the bottom of reactor 11 so that the feed material enters the reactor from the bottom and flows upwardly through the glass beads, the catalyst and the glass beads before exiting through the top of reactor 11. At the same time, oxygen supply valve 27 is opened to provide oxygen to the reactor 11 to oxidize the aromatic compound. During the process, the material in the feed stream and conduit 20, and the oxygen in conduit 23, is sufficiently pressurized as set forth above by pressure means 16 and 17 to maintain the feed material in the desired phase. That is, the reaction may proceed with the feed material in a liquid phase, and oxygen can be bubbled through the liquid, or all reactants may be in the vapor phase. Typically, when all reactants are in the vapor phase, a solid catalyst is used; and when one of the reactants is in a liquid phase, either a solid or a liquid catalyst can be used.

The feed material and oxygen are fed through reactor 11 at a rate sufficient to provide a liquid or weight hourly space velocity of greater than 1, more preferably greater than 2 and most preferably in the range of 5 to 20. As used herein and as known by those of skill in the art, weight (or liquid) hourly space velocity (WHSV or LHSV) is the amount of raw material (unit weight or volume) per unit weight or volume of catalyst per hour.

During the passage of feed materials through the reactors, the temperature within the reactors is maintained at the preferred temperature. This temperature will vary depending upon the specific feed material, the aldehyde being produced and the pressure within the reactors, among other possible factors. In general, the temperature and pressure are selected to achieve a desired reaction yield and to maintain the feed reactants in their gaseous or liquid form. Normally, the reaction temperatures for aromatic aldehyde production will be in the range of 50° C. to 400° C. For a benzaldehyde production process, the reaction temperature will be in the range of 50° C. to 400° C. and more preferably 100° C. to 300° C. and for a metatolualdehyde process, the reaction temperature will be in the range of 100° C. to 200° C.

Within reactor 11, the feed material reacts with the oxygen in the presence of the catalyst and at the preferred temperature to produce benzaldehyde, metatolualdehyde or other aromatic aldehyde. Some raw material may not react and it remains in its unoxidized form. With valve 52 closed and valve 54 open, this exit or product stream is then directed via conduit 58 to recovery means 61 where the desired aldehyde and the unoxidized raw material are separated from one another. Preferably, this separation/recovery process is a distillation process as is known in the art. Unoxidized aromatic compound may be recycled to reactors 11 and/or 12 via conduits 62 and 64, respectively.

With the method and apparatus as described above, selectivity rates to the desired aldehyde in excess of 80% or more can be achieved with conversion rates greater than 25%. With the recycle, this results in an extremely efficient method for producing aromatic aldehydes.

In the event reactor 11 requires maintenance or for some reason the reactor becomes plugged or the catalyst needs regeneration, second reactor 12 can be quickly and easily utilized without resulting in downtime and thus loss of production or production rate. To accomplish this conversion to reactor 12, reactor 12 can be brought up to the optimum temperature (by means of heater 42) and valve 24 can be opened to allow the flow of purging or other gas into the bottom of reactor 12 through the reactor and out through conduit 50. Once the optimum temperature has been reached and reactor 12 has been sufficiently purged, valve 19 is adjusted to direct the feed material from reservoir 14 into and through conduit 21 and through reactor 12; oxygen supply valve 27 is closed and oxygen supply valve 37 is opened. When this is done, valves 53 and 54 are closed and valve 55 is opened. The previously used reactor 11 is then isolated from the feed materials and can be isolated entirely from the system by closing valve 22 or can be provided with purging or regeneration material from reservoirs 25 and 26 if desired.

In the aldehyde production process of the preferred embodiment, the reaction time or reaction life cycle is greater than the catalyst regeneration time. Thus, a pair of reactors 11 and 12 is sufficient to provide a continuous aldehyde production process. As used herein, the term "reaction time" or "reaction life cycle" is the time during which acceptable reaction conditions exist (i.e., before catalyst regeneration is needed or plugging occurs) for selected feed materials and selected catalyst at specific reaction variables of temperature, pressure, WHSV and the like. The term "regeneration time" is the time needed to regenerate the selected catalyst. If the specific feed materials, catalyst and reaction variables are such that the reaction time or life cycle is less than the regeneration time, more than two reactors are used to maintain a continuous aldehyde production process.

Catalysts

For the production of an aldehyde by the above-described method, any suitable homogeneous catalyst may be used. Such catalysts include metal compounds that are soluble in the starting material or suitable solutions of such compounds, used at concentrations ranging from 200 to 2000 ppm. Preferred catalysts include copper and cerium esters, such as copper and cerium acetates and octoates. Other suitable homogeneous catalysts include soluble metal compounds selected from groups IB to VIIIB of the periodic table, i.e., salts of the transition metals, including such compounds as nitrates, perchlorates, halides, and sulfates. Soluble metallocenes may also be suitable.

Solid catalysts are equally suitable. Solid catalysts are typically those in which a catalyst is applied to a support material usually having a high surface area. Alternatively, the support material may be the catalyst. Suitable catalysts include, but are not limited to, metal or metal oxides such as the oxides of magnesium (MgO), titanium ($TiO_2$), zirconium ($ZrO_2$), zinc (ZnO), copper (CuO or $CuO_2$), cerium ($CeO_2$ or $Ce_2O_3$), or other lanthanides. In general, metals or metal oxides selected from groups IB to VIIIB of the periodic table may be useful in the practice of this invention.

Various catalyst supports are available from manufacturers such as United Catalyst Industries having various chemical composition, porosity, density, effective surface area, shape, size and cross section. Suitable catalyst supports include alumina, silica, zirconia and mixtures thereof as well as naturally occurring clays such as montmorillonite or kaolin. These support materials generally have effective surface areas ranging from about 20 to 500 $m^2$ per gram. Preferred substrates for use in the present invention include substrates such as titania ($TiO_2$), aluminum oxide ($Al_2O_3$), zinc oxide (ZnO), zirconium oxide ($ZrO_2$), or combinations of these oxides.

Preferred catalysts for the present invention include oxides of copper. A solution of the catalyst or a precursor to the catalyst is applied to an effective surface area of a support material such that there is substantially a theoretical monolayer of desired catalyst present. Further heat treatment of a catalyst precursor forms the catalyst. It has been found that a theoretical monolayer of catalyst optimizes the catalysis conditions. "Theoretical monolayer" refers to a film or layer of a material (catalyst) on a surface at a thickness of one molecule. As used herein, a substantially theoretical monolayer shall mean plus or minus 10% of a theoretical monolayer.

When applied, the catalyst or catalyst structure is expressed as weight percent of catalyst per unit weight of catalyst support. Conventionally, standard weight percentages of catalyst per unit weight of the support are prepared. For example, a 5% catalyst comprises 0.05 grams of catalyst per gram of catalyst support. Catalysts of 5%, 10% and other multiples of 5% are commonly prepared. This is accomplished by techniques including the incipient wetness method and spray or tumble-drying, as known to those of skill in the art.

Although conventional catalyst supports have effective surface areas ranging from about 20 to 500 $m^2$ per gram of support, the preferred catalyst support material for use in the production of aldehydes in the present invention has an effective surface area of about 20 to 500 $m^2$ per gram of support, more preferably about 25 to 300 $m^2$ per gram and most preferably about 30 to 200 $m^2$ per gram of support.

The above description and accompanying drawing are provided for the purpose of describing embodiments of the invention and are not intended to limit the scope of the invention in any way. It will be apparent to those skilled in the art that various modifications and variations can be made in the process for the production of an aldehyde without departing from the spirit or scope of the invention. Thus, it is intended that the present invention cover the modifications and variations of this invention provided they come within the scope of the appended claims and their equivalents.

What is claimed is:

1. A process for the production of an aldehyde comprising:

providing a compound of formula $R^1$—CX, wherein X is a group that leaves upon oxidation;

reacting $R^1$—CX and a source of oxygen to form $R^1$—COH, wherein the reacting occurs in the vapor phase at a temperature of from 100° C. to 200° C. and in the presence of a catalyst consisting essentially of one or more of copper oxide and copper esters, wherein $R^1$ is phenyl, which is unsubstituted or substituted by one or more identical or different radicals selected from $(C_1-C_{12})$-alkyl, $(C_1-C_{12})$-alkoxy, $(C_1-C_{12})$-alkanoyloxy, $(C_1-C_{12})$-alkanoyl, amino, hydroxyl, —CH$_2$—O—$(C_1-C_{12})$-alkyl, —NH—$(C_1-C_{12})$-alkyl, —NH—CO—$(C_1-C_{12})$-alkyl, or —S—$(C_1-C_{12})$-alkyl; and separating the $R^1$—COH.

2. The process of claim 1, wherein the source of oxygen is oxygen gas.

3. The process of claim 1, wherein the catalyst is cuprous oxide on a zirconia support.

4. The process of claim 3, wherein the catalyst is a monolayer of cuprous oxide.

5. The process of claim 3, wherein the cuprous oxide on the zirconia support is present at 2 to 20% by weight.

6. The process of claim 3, wherein the cuprous oxide on the zirconia support is present at 2 to 10% by weight.

7. The process of claim 1, wherein the catalyst is selected from copper octoate and copper acetate.

8. The process of claim 1, wherein X is —H$_3$.

9. The process of claim 1, wherein $R^1$ is meta-methylphenyl.

10. The process of claim 1, wherein the catalyst is a liquid catalyst.

11. The process of claim 1, wherein the catalyst is a solid catalyst.

12. The process of claim 1, wherein the reacting takes place in a tube reactor.

13. The process of claim 1, wherein the reacting takes place in two or more tube reactors connected in parallel.

14. The process of claim 13, further comprising stopping the reaction of $R^1$—CX and the source of oxygen in a first of the two or more tube reactors while passing the $R^1$—CX and the source of oxygen through a second of the two or more tube reactors and regenerating the catalyst in the first tube reactor.

15. The process of claim 1, wherein the process is a continuous process.

16. A method of preparing metatolualdehyde, comprising:

providing meta-xylene and a source of oxygen;

providing a tube reactor loaded with a catalyst consisting essentially of one or more of copper oxide and copper esters;

passing the meta-xylene and the source of oxygen through the tube reactor in the vapor phase at a temperature of between about 100° C. and 200° C.; and recovering the metatolualdehyde.

17. A method of preparing benzaldehyde, comprising:

providing toluene and a source of oxygen;

providing a tube reactor loaded with a catalyst consisting essentially of one or more of copper oxide and copper esters;

passing the toluene and the source of oxygen through the tube reactor in the vapor phase at a temperature of between about 100° C. and 200° C.; and recovering the benzaldehyde.

18. A process for the production of an aldehyde comprising:

providing a compound of formula $R^1$—CX, wherein X is a group that leaves upon oxidation;

reacting $R^1$—CX and a source of oxygen to form $R^1$—COH, wherein the reacting occurs in the vapor phase at a temperature of from 100° C. to 200° C., at a weight hourly space velocity of greater than one, and in the presence of a catalyst, wherein $R^1$ is phenyl, which is unsubstituted or substituted by one or more identical or different radicals selected from $(C_1-C_{12})$-alkyl, $(C_1-C_{12})$-alkoxy, $(C_1-C_{12})$-alkanoyloxy, $(C_1-C_{12})$-alkanoyl, amino, hydroxyl, —CH$_2$—O—$(C_1-C_{12})$-alkyl, —NH—$(C_1-C_{12})$-alkyl, —NH—CO—$(C_1-C_{12})$-alkyl, or —S—$(C_1-C_{12})$-alkyl; and separating the $R^1$—COH.

* * * * *